(12) United States Patent
Faure (10) Patent No.: US 9,655,676 B2
(45) Date of Patent: May 23, 2017

(54) METHOD OF PERCUTANEOUS LOCALIZED OR FOCAL TREATMENT OF PROSTATE LESIONS USING RADIO FREQUENCY

(75) Inventor: Andre Faure, Sarasota, FL (US)

(73) Assignee: Trod Medical, Paris (FR)

( * ) Notice: Subject to any disclaimer, the term of this patent is extended or adjusted under 35 U.S.C. 154(b) by 1202 days.

(21) Appl. No.: 13/117,716

(22) Filed: May 27, 2011

(65) Prior Publication Data

US 2011/0288541 A1 Nov. 24, 2011

Related U.S. Application Data

(63) Continuation of application No. 12/992,702, filed as application No. PCT/EP2009/055984 on May 18, 2009, now Pat. No. 9,220,892.

(Continued)

(30) Foreign Application Priority Data

Dec. 8, 2008 (EP) .................... 08171007

(51) Int. Cl.
| | |
|---|---|
| *A61B 18/12* | (2006.01) |
| *A61B 18/14* | (2006.01) |
| *A61B 18/00* | (2006.01) |
| *A61B 90/11* | (2016.01) |
| *A61B 90/00* | (2016.01) |

(52) U.S. Cl.
CPC ........... *A61B 18/1482* (2013.01); *A61B 90/11* (2016.02); *A61B 2018/00547* (2013.01); *A61B 2018/1425* (2013.01); *A61B 2018/1435* (2013.01); *A61B 2090/378* (2016.02)

(58) Field of Classification Search
CPC ................. A61B 2019/5276–2019/566; A61B 2018/00547; A61B 2018/00982; A61B 34/00; A61B 2034/101; A61B 2034/104; A61B 2034/107; A61B 2034/108;
(Continued)

(56) References Cited

U.S. PATENT DOCUMENTS

| | | |
|---|---|---|
| 5,507,743 A | 4/1996 | Edwards et al. |
| 5,676,662 A | 10/1997 | Fleischhacker et al. |

(Continued)

FOREIGN PATENT DOCUMENTS

| | | |
|---|---|---|
| DE | 19713797 A1 | 10/1997 |
| WO | WO 00/35531 A1 | 6/2000 |

(Continued)

*Primary Examiner* — Joseph Stoklosa
*Assistant Examiner* — Eunhwa Kim
(74) *Attorney, Agent, or Firm* — Reinhart Boerner Van Deuren P.C.

(57) ABSTRACT

The present invention is related to a method of realizing percutaneous (transperineal) ablation of prostate tumor regions, using a radio frequency based coiled device. A bipolar electrode assembly comprising an outer helical electrode and an inner electrode arranged concentric with the outer helical electrode, wherein prior to applying radio frequency energy, at least the outer helical electrode is inserted percutaneously into the prostate. An image of the prostate and of the outer helical electrode as inserted is acquired, such that the outer helical electrode is visualized on the image. A graphical representation of a target position of the bipolar electrode assembly is superposed on the image.

19 Claims, 10 Drawing Sheets

Related U.S. Application Data (60) Provisional application No. 61/053,788, filed on May 16, 2008.

(58) Field of Classification Search
CPC .... A61B 2018/1435; A61B 2018/1846; A61B 2018/126
USPC .................................................. 606/33–52
See application file for complete search history.

(56) References Cited

U.S. PATENT DOCUMENTS

| | | |
|---|---|---|
| 5,921,982 A | 7/1999 | Lesh et al. |
| 5,928,229 A | 7/1999 | Gough et al. |
| 6,165,170 A | 12/2000 | Wynne et al. |
| 6,167,292 A | 12/2000 | Badano et al. |
| 6,497,704 B2 | 12/2002 | Ein-Gal |
| 2001/0041838 A1* | 11/2001 | Holupka et al. ............ 600/439 |
| 2002/0016540 A1* | 2/2002 | Mikus .................. A61B 18/02 600/407 |
| 2002/0049439 A1 | 4/2002 | Mulier et al. |
| 2002/0147446 A1 | 10/2002 | Ein-Gal |
| 2002/0156361 A1* | 10/2002 | Popowski ............. A61B 5/417 600/407 |
| 2004/0002699 A1* | 1/2004 | Ryan et al. .................... 606/27 |
| 2005/0085807 A1 | 4/2005 | Venturelli |
| 2006/0052770 A1* | 3/2006 | Mulier et al. .................. 606/41 |
| 2006/0258933 A1* | 11/2006 | Ellis et al. .................... 600/407 |
| 2007/0027448 A1 | 2/2007 | Paul et al. |
| 2007/0179494 A1 | 8/2007 | Faure |
| 2008/0071262 A1 | 3/2008 | Azure |
| 2011/0071515 A1 | 3/2011 | Faure et al. |

FOREIGN PATENT DOCUMENTS

| | | |
|---|---|---|
| WO | WO 2004/100812 A1 | 11/2004 |
| WO | WO 2007/144004 A1 | 12/2007 |

* cited by examiner

METHOD OF PERCUTANEOUS LOCALIZED OR FOCAL TREATMENT OF PROSTATE LESIONS USING RADIO FREQUENCY

CROSS-REFERENCE TO RELATED PATENT APPLICATIONS

This patent application is a continuation-in-part of U.S. application Ser. No. 12/992,702 filed on Nov. 15, 2010 which is a U.S. Nationalization of PCT/EP2009/055984 filed on May 18, 2009 which claims priority to European Patent Application No. 08171007.1 filed on Dec. 8, 2008 and U.S. Provisional Application No. 61/053,788 filed on May 16, 2008. The entire teachings and disclosure of all of the applications referenced in the preceding sentence are incorporated herein by reference thereto.

FIELD OF THE INVENTION

The present invention generally relates to treatment of prostate lesions, such as prostate cancer, by percutaneous techniques. More particularly, the present invention relates to the treatment of prostate lesions by radio frequency ablation.

BACKGROUND OF THE INVENTION

Treating lesions within the prostate is a difficult task due to the organ's complex anatomy. Due to the fact that the prostate is surrounded by important organs, such as nerve bundles and the rectum, as well as is crossed by the urethra, extreme precision is required in treating any lesion within the prostate, if collateral damages are to be avoided.

At present, brachytherapy and cryoablation, for example, are used as percutaneous techniques for treating prostate lesions. Percutaneous techniques have the advantage of minimizing surgical intervention, allowing a reduced recovery time for the patient.

Brachytherapy uses a multitude of radio-active seeds that are implanted and which destroy the tissue over a long time period (some months). Implanting the radioactive seeds is performed through the insertion of needles which are prone to deviation when inserted through tissue. Operator's skill is therefore required to minimize deviation and the locations of implant are generally monitored with an ultrasound imaging probe. The area of destruction depends on the seeds' intensity of radioactivity, which makes it possible to estimate (using a complex calculation software) the area that will be destroyed. As many seeds are implanted so as to ensure that the entire prostate gland is destroyed. However, the radio-active seeds can move over time within the tissue, resulting in a high rate of collateral damage (mainly impotence). Therefore, brachytherapy has a poor accuracy when it comes to delimiting the region to be destroyed. In addition, as radioactive seeds destroy tissue within months, brachytherapy is not well suitable for localized (or focal) destruction, because of the risk of cancer dissemination during insertion of the probes.

In cryoablation, a cryogenic fluid (most often an Argon source) is used to destroy tissue by freezing. A number of probes are percutaneously inserted in the prostate. The probes are connected to a cryogenic fluid (argon) generator, which, once activated, cools down the probes and the surrounding tissue to destroy it. The destruction effect starts from the probe and expands, forming a kind of expanding ice ball. The ice ball continues to expand even after the generator is turned off. It is therefore extremely difficult to control exactly the area of destruction. Moreover, at the boundary of the ice ball, the freezing can be reversible (the cells are not totally destroyed). An ultrasound imaging device may be used to monitor the location of the cryogenic probes, but doesn't allow monitoring the area that is destroyed. Also with this technique, the collateral damage rates (mainly impotence and rectal dysfunction) are very high.

There exists hence a need in the art to provide an alternative percutaneous technique for treating prostate lesions and which is more precise, and reduces the occurrence of collateral damage, mainly impotence and incontinence.

It is therefore an object of the present invention to provide a method of percutaneous treatment of prostate lesions, which is capable of not only precisely delimit the region that is destroyed, but also which allows to precisely predict beforehand—before imparting any damage to tissue—the region or area that will be destroyed. It is another object of the present invention to provide a method of percutaneous treatment of prostate lesions, enabling to easily and directly verify—before starting with the actual treatment—the correspondence between the volume/region that is destroyed and the volume/region that one plans to destroy.

BRIEF SUMMARY OF THE INVENTION

According to an aspect of the invention, there is provided a method of percutaneous treatment of a prostate lesion using radio frequency as set out in the appended claims.

According to an aspect of the invention, there is provided a method of percutaneous treatment of a prostate lesion using radio frequency, comprising the following steps. With an imaging device an image of a patient's prostate is acquired. Within the prostate at least one location to be treated is identified. The location to be treated may optionally be represented on the image of the prostate. A bipolar electrode assembly for radio frequency treatment is selected, the assembly comprising an outer helical electrode and at least one inner electrode arranged concentric with the outer electrode. A planned target region is represented on the image of the prostate, the planned target region corresponding to a target position of at least an active part of the outer helical electrode. The planned target region is placed such that it encloses the location to be treated. The bipolar electrode assembly is positioned in proximity of the patient's perineum and in alignment with the planned target region's position. At least the outer helical electrode of the bipolar electrode assembly is inserted percutaneously into the prostate. The inserted outer helical electrode is captured with the ultrasound imaging device. The inserted, captured electrode is represented on the image of the prostate together with the planned target region so as to obtain a direct verification of the degree of match between the position of the outer electrode and the planned target region.

According to a second aspect of the invention, there is provided a method of percutaneous treatment of a prostate lesion of a patient by applying radio frequency energy by means of a bipolar electrode assembly comprising an outer helical electrode and an inner electrode arranged concentric with the outer helical electrode, wherein prior to applying radio frequency energy, at least the outer helical electrode is inserted percutaneously into the prostate. An image of the prostate and of the outer helical electrode as inserted is acquired, such that the outer helical electrode is visualized on the image. A graphical representation of a target position of the bipolar electrode assembly is superposed on the image.

BRIEF DESCRIPTION OF THE DRAWINGS

FIGS. 1A and B represent flow diagrams of steps according to embodiments of the invention.

DETAILED DESCRIPTION OF THE INVENTION

This description provides examples not intended to limit the scope of the appended claims. The figures generally indicate the features of the examples, where it is understood and appreciated that like reference numerals are used to refer to like elements. Reference in the specification to "one embodiment" or "an embodiment" or "an example embodiment" means that a particular feature, structure, or characteristic described is included in at least one embodiment described herein and does not imply that the feature, structure, or characteristic is present in all embodiments described herein. It is to be understood that embodiments of the invention described herein are capable of operation in other sequences than described or illustrated herein.

The present invention encompasses the use of a bipolar helical electrode assembly for destroying a target volume within the prostate by radio frequency ablation. Radio frequency ablation destroys living tissue by heating. Bipolar helical electrodes for radio frequency ablation are known.

Figure 3:
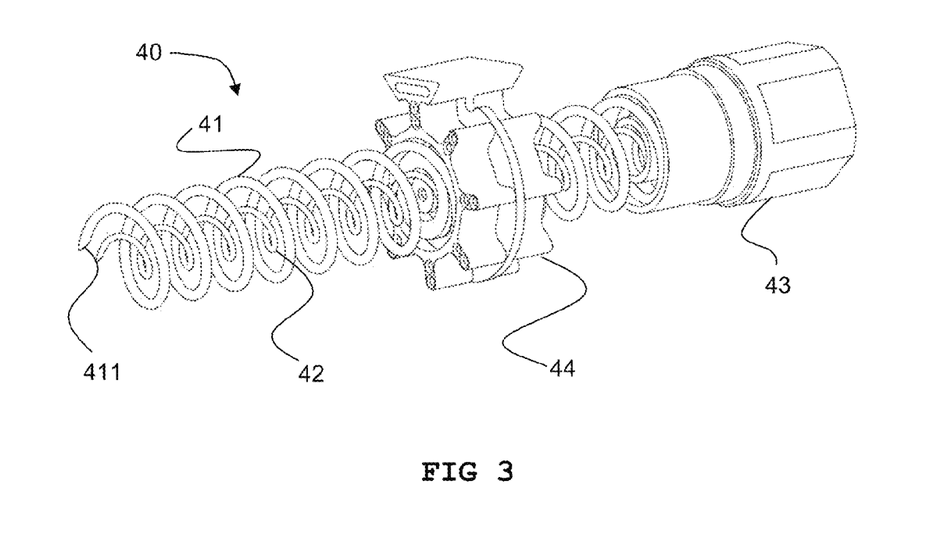
FIGS. 3 and 4 represent embodiments of bipolar helical electrode assemblies as may be used in methods of the invention.
Figure 4:
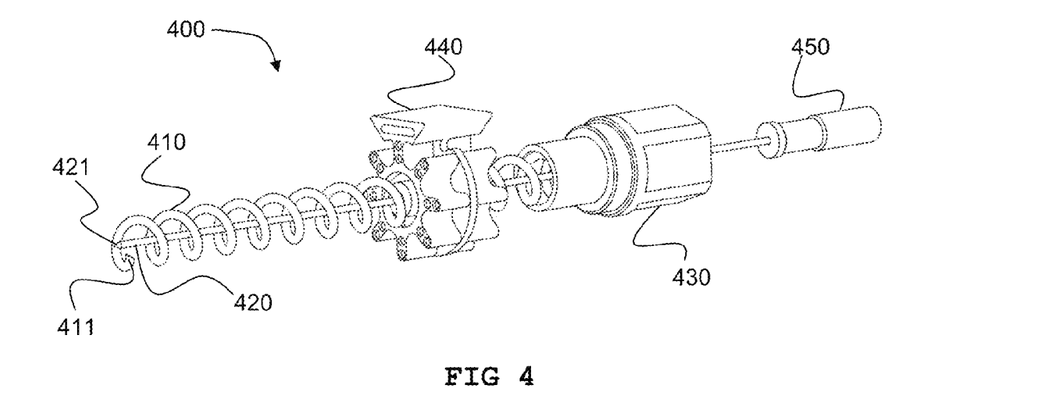

Bipolar radio frequency (RF) electrode assemblies, also referred to herein as surgical instruments, as used in the present invention, comprise at least one helical electrode. In an embodiment, they comprise two helical electrodes 41 and 42 as represented in FIG. 3. Additional helical electrodes may be provided as desired. Alternatively, the bipolar electrode assembly is formed by one or more helical electrodes 410 and a straight electrode 420 as represented in FIG. 4. An electrode guiding device 44, 440 may additionally be provided.

Electrode assemblies 40, 400 comprise at least two concentrically arranged electrodes 41-42, 410-420 having different diameters. The outermost electrode 41, 410 is always helical, since it defines the external limit of the lesion that will (can) be created. All electrodes have elongated structure with a tip 411, 421 at a distal end configured to penetrate through tissue and hence suitably sharp. At the proximal end, the electrodes are provided with a connector (not shown) by which the electrodes are connectable to a radio frequency generator to function as poles of a bipolar electrode. Connection, such as by wire, between the different electrodes and the generator can be removed when not needed, such as to facilitate insertion of the electrodes inside the patient. When the assembly comprises three or more electrodes, each one with its proper support, they are all connectable to the RF generator, but such that only two can be active simultaneously to function as bipolar electrode. Switching can be effected either manually, such as by changing a connector plug between electrodes, or through a controller or electric switch.

Referring to FIG. 3, outer helical electrode 41 and inner helical electrode 42 share a same longitudinal axis (i.e. they are concentric), have same pitch, and have different diameters. Both outer helical electrode 41 and inner helical electrode 42 comprise multiple helical windings of same diameter and pitch. Such an arrangement results in a constant and uniform gap between the helices of the different electrodes, which helps in obtaining a uniform heating of the treatment zone.

In an embodiment, both the helical electrodes 41 and 42 are fixed to a base 43 by any suitable means, such as by gluing. Each of the helical electrodes 41, 42 makes contact with a connector (not shown) which can be electrically coupled to a radio frequency generator.

Referring to FIG. 4, a central, straight electrode 420 is arranged inside an outer helical electrode 410. Central electrode 420 may have a length corresponding to, or larger than that of the helical electrode 410. Central electrode 420 may be concentric with helical electrode 410.

Each electrode 41, 42, 410, 420 comprises an active part arranged on an insulated support. The active part preferably extends continuously along a length of the electrode corresponding to at least one pitch of the helix of the (inner or outer, as the case may be) electrode. Both the active part and the insulated support can be helical. In an embodiment, the active parts of the inner and outer electrodes have same length.

In an embodiment, the helical electrode 410 is fixed to a base 430 by any suitable means, such as by gluing, while the central electrode 420 is translatable (linearly) relative to the base 430 and the helical electrode 410. In such case, the base 430 is provided with a through-hole for insertion of the central electrode 420.

Connectors for coupling to a radio frequency generator may be provided in the base 43, 430. The central electrode 420 of FIG. 4 may comprise at its proximal end its proper base 450, which may further be provided with such an electrical connector for coupling to a radio frequency generator.

The bipolar RF surgical instrument can be of the type described in U.S. application Ser. No. 10/556,770 which is incorporated herein by reference.

The RF helical electrodes 41, 42, 410 and/or the straight electrode 420 have sharp distal tips 411, are not deformable, and rigid. They are "dry electrodes", i.e. not hollow and not able to deliver a conductive fluid. Preferably, they are made of a biocompatible metal, such as biocompatible stainless steel. By way of example, they can be made of surgical stainless steel type 304 or type 316.

The base 43, 430, 450 may have a hollow shape, and be made of a biocompatible polymeric material, for example poly-ether-ether-ketone (PEEK), polycarbonate or polyamide.

In an example embodiment, the electrodes are coated partially along the length with an insulating polymeric compound, for example PTFE or polyester, with the exception of the active part. The active part can be situated at the distal tip of the electrode.

The helical electrodes 41 and 42 may be formed of a wire or rod of same or different thickness (diameter). Preferably, the thickness is between about 1 mm and about 2 mm, such as about 1.2 mm. The helical electrodes may have a length corresponding to at least 15 turns or windings of the helix, or a length of about 150 to 200 mm. The helix is preferably a right-handed helix and preferably has a constant diameter. The pitch of the helix may fall in the range between about 5 mm and about 20 mm. The helical electrodes 41, 42 and 410 have typically an outer diameter (of the helix) comprised between about 8 mm and about 24 mm.

In an embodiment, bipolar helical electrode assemblies 40, 400 according to the invention are for single use and disposable.

Each electrode of the bipolar electrode assembly can be activated independently of the other(s) to act as one pole of the bipolar electrode. The term "activated" refers to that a current is applied into the electrode.

Bipolar electrode assemblies according to the present invention are configured not to move during radio frequency treatment. No conductive liquid is injected for enhancing radio frequency treatment. These measures, together with the structure itself of the electrode assembly allow for confining the lesion within a cylinder centered around the outermost helical electrode and having a radius less than 1 mm larger than the outer radius of the outermost helical electrode.

In embodiments, such as the one represented in FIG. 4, wherein a straight needle 420 is used as central (inner) electrode, and a helical electrode 410 is wrapped concentrically around it, the needle 420 can be positioned with its tip 421 aligned with the tip 411 of the helical electrode 410. When needle 420 is freely translatable along its longitudinal axis, tip 421 can be moved a bit ahead of tip 411 to provide for a rounded (convex) border of the lesion at the electrode tip.

Bipolar helical electrode assemblies as contemplated in the present invention advantageously comprise an electrode guiding device 44, 440, 441, embodiments of which are represented in greater detail in FIGS. 5 through 8.

Electrode guiding devices of the RF electrode assemblies according to the invention comprise a main body 7 comprising at least two through-holes 8 and 81 (FIG. 5), or 8 and 82 (FIG. 6), and may comprise even three or more through-holes 8, 81 and 82 (FIG. 7), all of which extend through the body 7.

Figure 8:
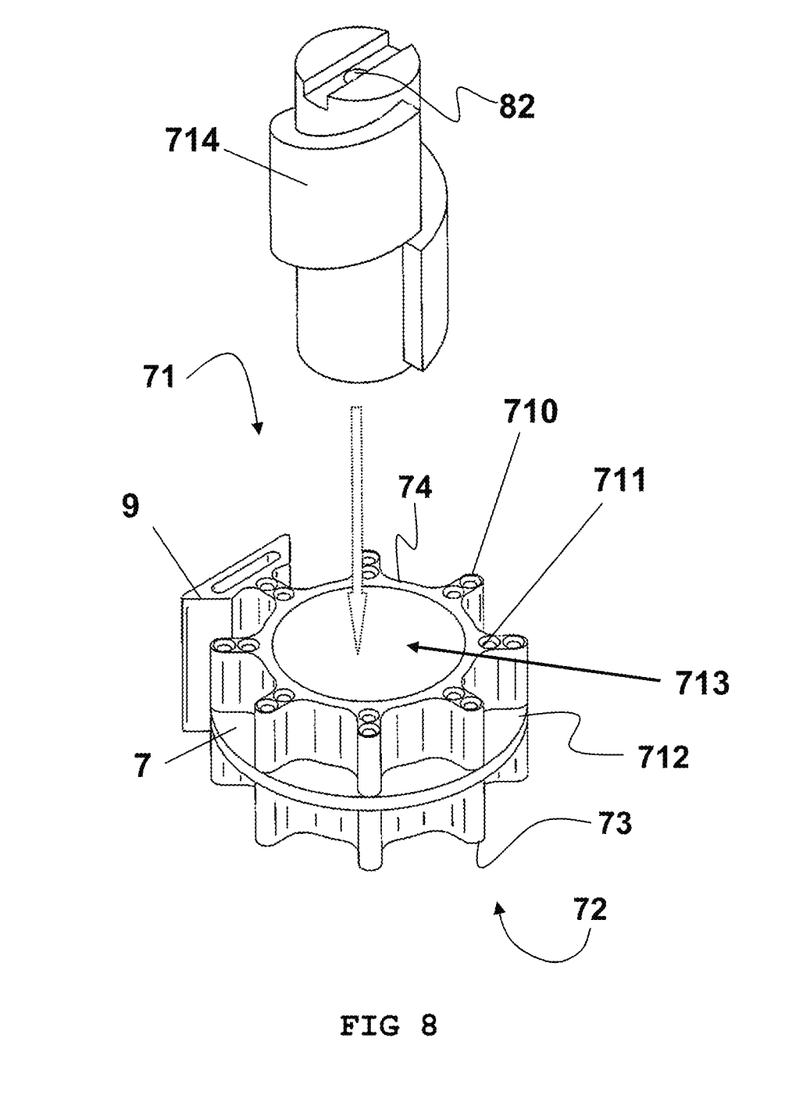
FIG. 8 represents an exploded view of the guide of FIG. 5.

Referring to FIG. 8, the main body 7 comprises a front side 71, a back side 72, a proximal end 73 and a distal end 74.

The main body 7 may have any suitable shape. In an embodiment, it is substantially cylindrical with its axis oriented along proximal-distal direction. It may also have, for example, a prismatic shape with polygonal or square base. The main body 7 can be made of metal, or polymeric material. For example, it can be made of titanium, stainless steel, poly-ether-ether-ketone (PEEK), polycarbonate, or polyamide.

Figure 5:
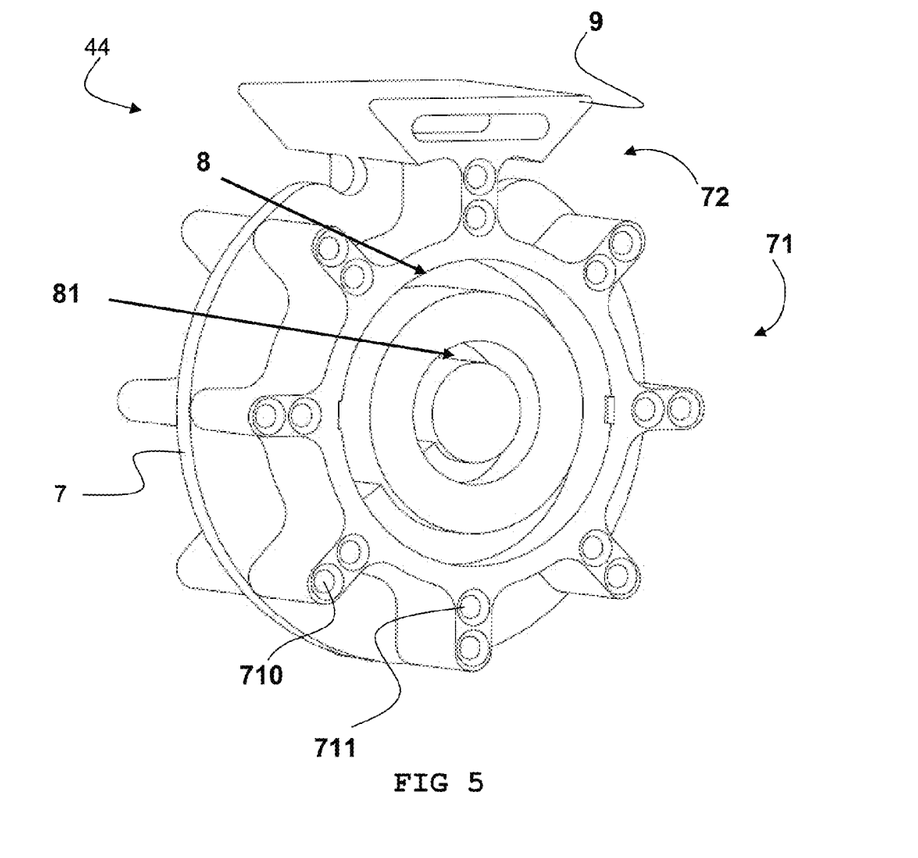
FIG. 5 represents a guide for the helical electrodes as represented in FIG. 3.
Figure 6:
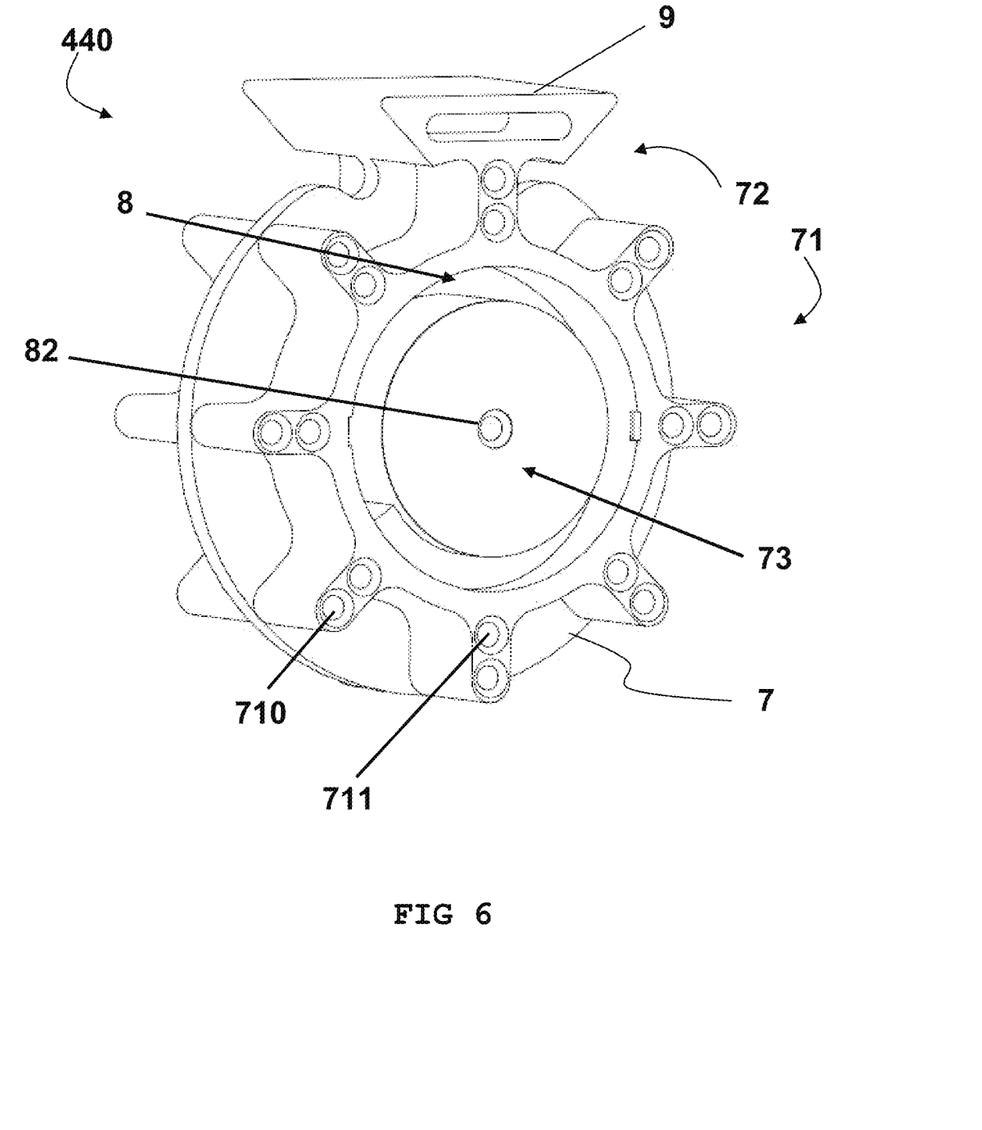
FIG. 6 represents a guide for the assembly of helical and straight electrodes as represented in FIG. 4.
Figure 7:
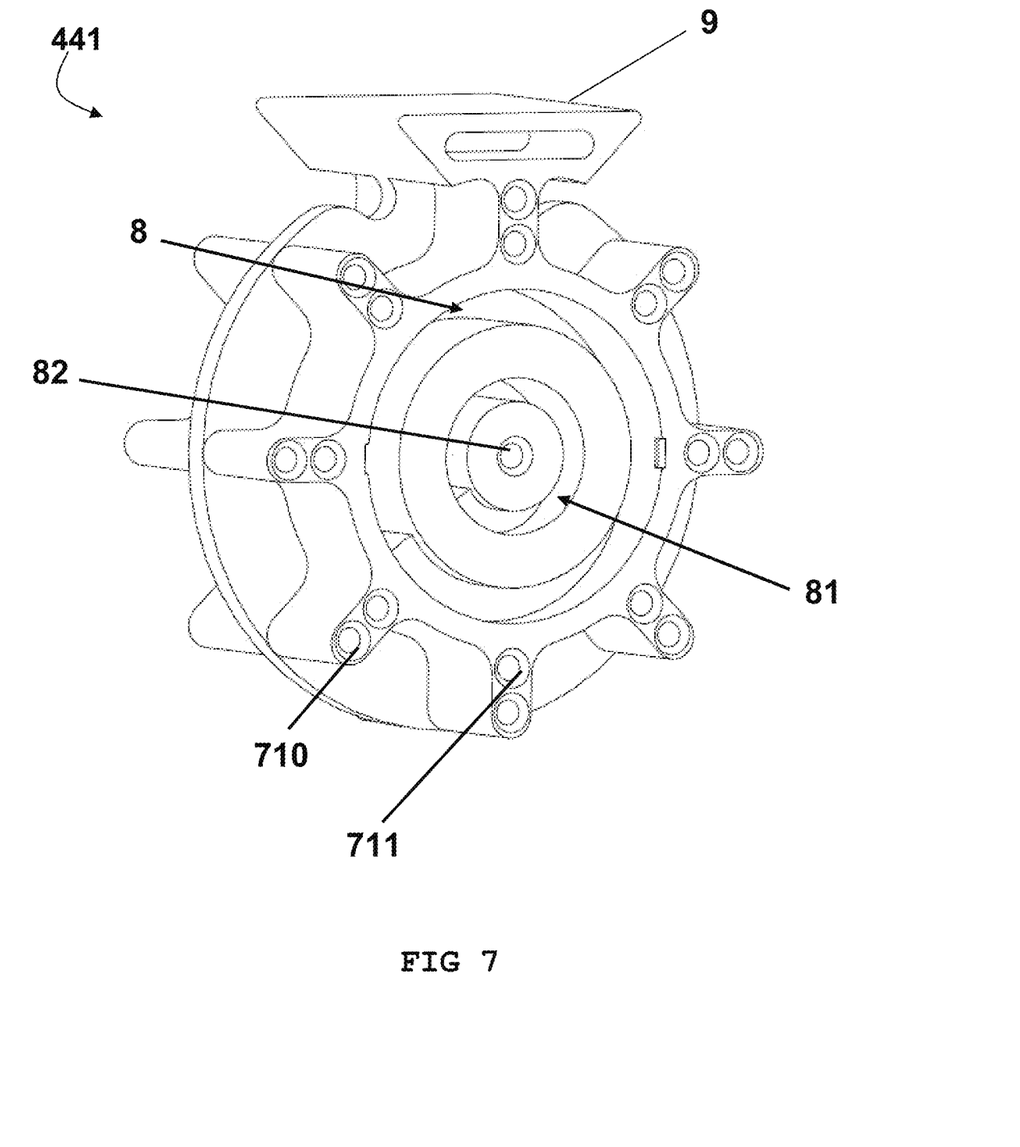
FIG. 7 represents yet another guide for assemblies with one or two concentric helical electrodes with or without a central straight electrode.

Through the main body 7, and on the surfaces defined by the front side 71 and the back side 72, the holes 8, 81, and/or 82 have a shape and a diameter which correspond substantially to the shape and diameter of the electrodes 41-42, or 410-420, and such that each electrode can pass through its corresponding hole by either helical movement (for helical electrodes) or axial movement (for straight needle). Electrodes can hence be inserted through corresponding holes of the guiding device and can move relative to it. Electrode guiding device 44, 440 can move relative to base 43, 430 respectively as well. Such electrode guiding devices provide the advantage of maintaining the dimensional stability of the electrodes by preventing their deformation and radial movement during perforation of the skin and penetration into the patient. This helps in confining the lesion that is created.

In an example embodiment, represented in FIG. 5, the main body 7 of the guiding device comprises two helical holes 8 and 81.

In another example embodiment, represented in FIG. 6, the main body 7 of the guiding device comprises one helical 8 and one straight hole 82.

In yet another example embodiment, represented in FIG. 7, the body 7 comprises two helical holes 8, 81 and one straight hole 82.

However, the number of holes and their shape are not limited to those disclosed here as examples. The guiding device may comprise as many holes, and as different, as there are electrodes in the corresponding electrode assembly.

The main body 7 of the electrode guiding device has an overall size (external dimensions) at least larger than the external diameter of the outermost helical electrode. Preferably, the body 7 has a size and a shape enabling its use with a catheter.

In an embodiment of electrode guiding devices according to the invention, as represented in FIGS. 5-8, the main body 7 comprises at least one supplementary through-hole 710 arranged at the periphery of the body 7. Preferably, the holes 710 are straight and several of them are provided in a tangential manner at the periphery of the main body 7. A second series of straight through-holes 711 may be additionally provided, laid in a tangential manner at the periphery of the main body 7, but more inwards than the first series of holes 710. Both the first series of holes 710 and the second series of holes 711 may be provided on circles around the periphery of the main body 7, the circle corresponding to the first series being of larger diameter than the circle corresponding to the second series.

The supplementary holes 710 and/or 711 may guide any other electrode, anchoring member, or needle, such as a straight needle, for example for introducing a chemotherapeutic agent into the tissue before, during, or after ablation, or a needle biopsy aspiration device, or any sensor, such as temperature sensors, or any optical device, or illumination fibres.

When the tissue to treat is exceeds the size of the largest helix formed by the outermost helical electrode 41 or 410, at least one straight RF electrode can be used, said straight RF electrode being guided precisely where wanted, thanks to the specific arrangement of the supplementary holes 710 and/or 711 into the guiding device 44, 440, 441. To widen the volume of tissue to treat, the RF generator is connected to either the outermost helical electrode 41, 410 and the supplementary straight electrode (not shown) arranged in one of holes 710, 711, or between the central member 420 and the supplementary straight electrode (not shown) for providing activation of the electrode pair in a bipolar fashion.

Optionally, the guiding device 44, 440, 441 further comprises a fixing part 9, to allow the guiding device to be handheld, or to be fixed to a percutaneous surgical instrument or a laparoscopic surgical instrument, or any stable frame.

The main body 7 of the electrode guiding device may be made either of one piece, or out of an assembly of two or more elements. The one or different pieces of the main body 7 may be produced by any suitable method, for example by extrusion, by moulding or by rapid prototyping techniques, such as stereolitography.

In an embodiment and referring to FIG. 8, the through-holes 8, 81 and/or 82 are formed by the assembly of an outer body 712, having a circular opening 713, and a threaded rod 714 engaged in said circular opening 713. The thread of rod 714 forms the helical hole 8, 81 when assembled and corresponds to the helical shape (pitch, diameter) of the corresponding electrode that is configured to pass along, thereby following the thread. Also, the diameter of circular opening 713 corresponds to the external diameter of the corresponding helical electrode. The external diameter of rod 714 can be a little oversized relative to the diameter of opening 713, so that it tightly fits in it.

The threaded rod 714 can further comprise a hole 82 in its center. In case of two or more helical through-holes 8, 81 such as represented in FIGS. 5 and 7, these may be provided by an assembly of two or more threaded rods 714 into one another, such that the outer rod has an opening along its axis in which the inner rod tightly fits and all rods 714 can be concentric.

Treating Prostate Lesions

Figure 1:
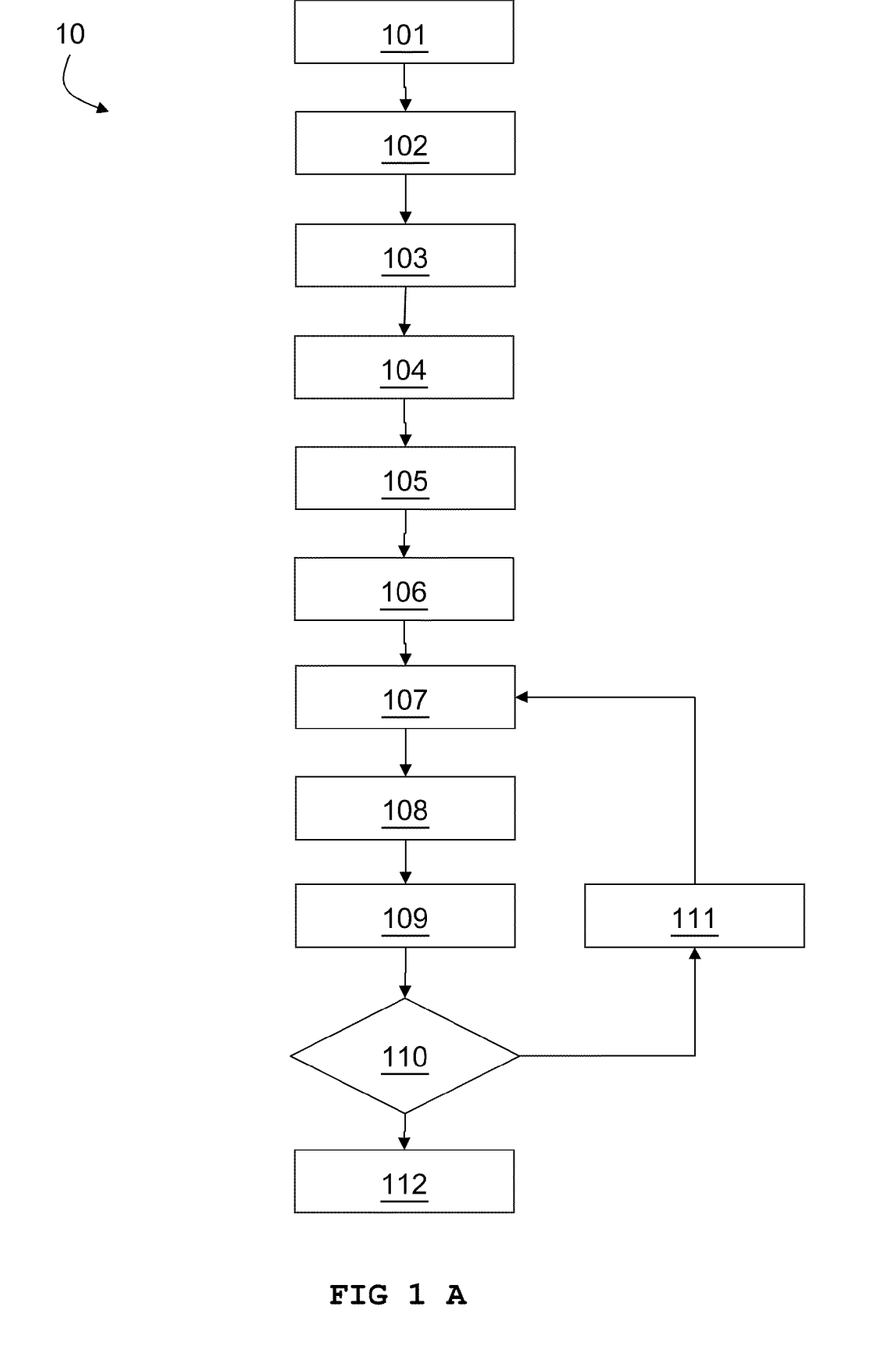
Figure 2:
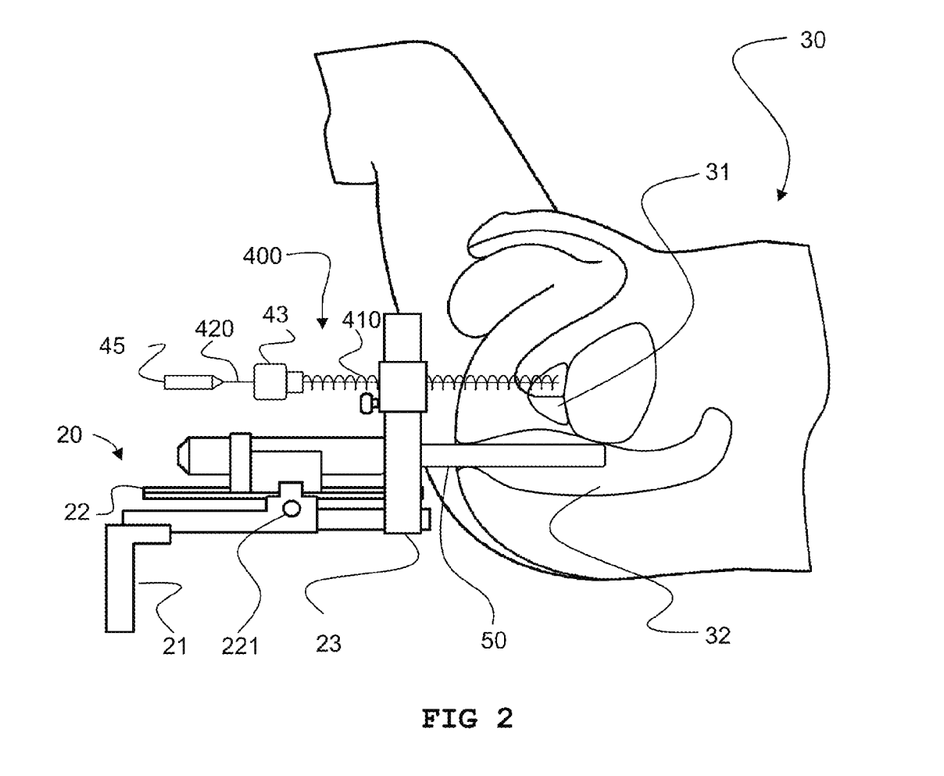
FIG. 2 represents schematically an example embodiment of a set up as used in methods of the invention.

Above described electrode assemblies are advantageously used in methods of treatment of prostate lesions using radio frequency. Referring to FIG. 1A, there is shown a schematic flow diagram 10 of a method of percutaneous treatment of a lesion within the prostate gland of a patient, according to the present invention. Example embodiments of the method will be explained with reference to FIG. 2, showing a setup for carrying out the method.

In a first step 101, an image of a prostate 31 of a patient 30 is acquired. In a preferred embodiment, the image is acquired with an ultrasound imaging device. The ultrasound imaging device is preferably a rectal ultrasound probe 50, which is inserted into the rectum 32 of the patient 30 to acquire ultrasound images of the prostate region. In an example embodiment, the imaging device acquires two-dimensional images corresponding to sections taken along a sagittal plane, a transverse plane, or both. The imaging device may acquire a sequence of two-dimensional (parallel) images (or scans) of the prostate at predetermined intervals to obtain a mapping of the prostate gland 31.

In an embodiment, the ultrasound imaging device 50 is mounted on a motion guide or stepper 22, preferably a linear motion guide. This enables to obtain absolute positioning information of the imaging device and hence of the prostate with reference to an external (to the patient) co-ordinate origin. Referring to FIG. 2, a linear motion guide 22 is shown, which can move forward or backward by turning control knob 221. The linear motion guide is fixed on a bracket or table 21.

Figure 10:
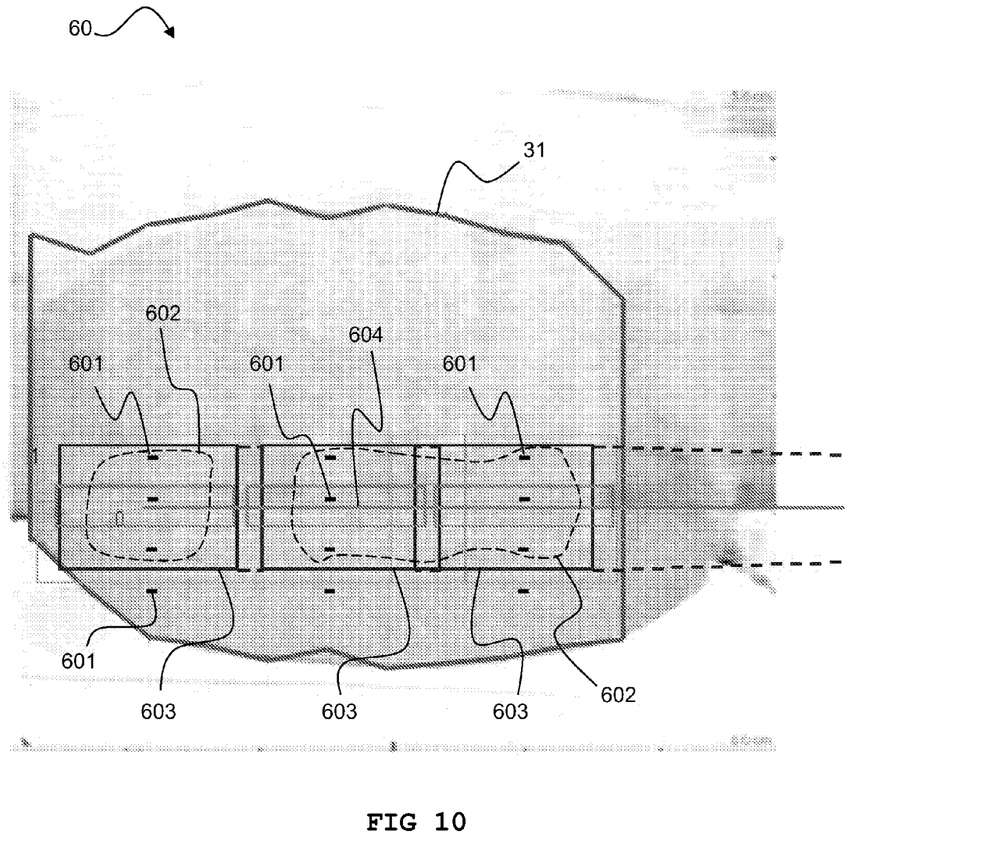
FIG. 10 represents an ultrasound image of a longitudinal section of a prostate, on which planned target regions of a helical electrode assembly are superposed.

In a step 102, the image(s) of the prostate gland 31 acquired in step 101 are displayed on a graphical display, which can be a computer monitor, or a display of the imaging device used in step 101. Acquired images can be displayed as sectional images (two-dimensional), or can be combined to obtain a three-dimensional image of the prostate gland 31. Such an ultrasound image 60 of a longitudinal section of the prostate 31 is shown in FIG. 10.

In a step 103, at least one region to be treated, such as a cancer zone, is identified within the prostate. In an embodiment, identifying prostate's cancer zone(s) to be treated (i.e. positive cores) is done with classic biopsy techniques, such as transperineal mapping biopsy, or transrectal biopsy. In addition, or alternatively, MRI imaging can be used.

In an embodiment, the (ultrasound) imaging device 50 is used to determine the positions where a biopsy is performed, such as by acquiring the position of biopsy locations, such as locations where biopsy needles are inserted. This position may be mapped on the acquired image of the prostate (image of step 101). Referring to FIG. 10, positions 601 of biopsy locations have been mapped on to image 60. In an embodiment, the (ultrasound) imaging device 50 is used as a guidance tool for correct positioning of the biopsy needles, in order to prevent deviation during insertion. In such case, either the acquired position (through the imaging device), or the predetermined position, calculated based on the point of insertion of the needle at the perineum and the depth of insertion, may be mapped (or merged) on the acquired image of the prostate.

In an embodiment, a zone enclosing locations with positive biopsy results (i.e. cancer positive cores) is defined as a region to be treated. Alternatively, one identifies the locations yielding positive biopsy results and uses these locations as sufficient indication of the one or more regions to be treated, i.e. no enclosing zone need be drawn around those locations.

In general, time is needed to obtain the biopsy results, so step 103 may not be carried out on the same day as other steps. This is shown in the flow diagram 100 of FIG. 1B. Step 103 may be carried out independently and its results are used in step 104. All other method steps in FIG. 1B are identical to the method represented in FIG. 1A.

Referring to FIGS. 1A and B, in a step 104, the region(s) to be treated as determined in step 103 may be represented on the image of the prostate on the graphical display. Referring to FIG. 10, a zone 602 is drawn around positions 601 yielding positive biopsy. In an embodiment, biopsy locations yielding a positive result are represented on the acquired image of the prostate differently than biopsy locations having a negative result. The locations with negative biopsy result may or may not be represented on the image on the graphical display.

Now that the region(s) 602 to be treated have been identified and represented, a bipolar helical electrode assembly for radio frequency treatment is selected in a step 105. Suitable bipolar electrode assemblies have been described above with reference to FIGS. 3 and 4. Such assemblies 40, 400 comprise an outer helical electrode 41, 410 and at least one inner electrode 42, 420 arranged inside the helix of the outer helical electrode 41, 410. In an embodiment, the outer helical electrode 41, 410 comprises multiple windings or coils of a helix. Preferably, the multiple windings have same pitch and diameter. The inner and outer electrodes are preferably arranged concentrically. A concentric arrangement helps in obtaining a uniform heating of the treatment zone, since the distance between the two electrodes is constant.

In an example embodiment, in step 105 a bipolar helical electrode assembly 40, 400 with an outer helical electrode 41, respectively 410 of predetermined size (diameter of the coil and length of the active part of the electrode) is selected based on the size and location of the region that will be subjected to treatment (region defined in step 103 and/or 104).

Once the size of the bipolar helical electrode assembly that will be used for treatment has been determined, a target position within the prostate is determined. According to the invention, the target position is determined with the aid of the captured image 60 of the prostate, and based on the region to be treated identified in step 103. That is, as shown in FIG. 10, a graphical representation 603 of the active part of the selected outer helical electrode is placed (superposed, by image fusion) on the image 60 of the prostate on the graphical display in a step 106. This graphical representation 603 will be referred to as the planned target region for treatment. Preferably, the planned target region encloses at least in part the region 602 subject to be treated as defined and identified in step 103. As shown in FIG. 10, more than one planned target region 603 may be determined. However, each planned target region corresponds to one surgical intervention, in the sense that the electrode assembly should be repositioned between different planned target regions.

The planned target region should preferably have a size corresponding to the area or volume enclosed or wrapped by the outer helical electrode. In practice, the planned target region should at least represent the diameter and/or length of the (active, non-insulated part of the) outer helical electrode. This may have a box-like or ring-like (in two-dimensional images), or cylindrical (in three-dimensional representations) shape.

In addition to a graphical representation 603 of the outer helical electrode, a target position 604 for the selected inner electrode may be graphically represented as well, such as shown in FIG. 10.

When one is working with multiple images of the prostate, one may position the planned target region on one image and a computer program may calculate and/or show the position of the planned target region on the other images, so that the planned target region is represented graphically on all images of interest.

In a step 107, the bipolar helical electrode assembly 40, 400—selected in step 105—is positioned close to the skin of patient 30, in proximity of the patient's perineum. This will be the starting position, from which the inner and outer electrodes will be inserted into the patient 30. Assembly 40, 400 may be positioned according to a projection of the planned target region to outside the patient 30, along the orientation direction (insertion direction) of the electrode assembly. In an embodiment, a rectal ultrasound probe 50 is used and the external (starting) position of electrode assembly 40, 400 can, in addition, be determined with the aid of a computer program, by considering the axis of the electrode assembly (i.e. the direction of insertion) to be parallel to the orientation of the rectal probe 50.

Figure 9:
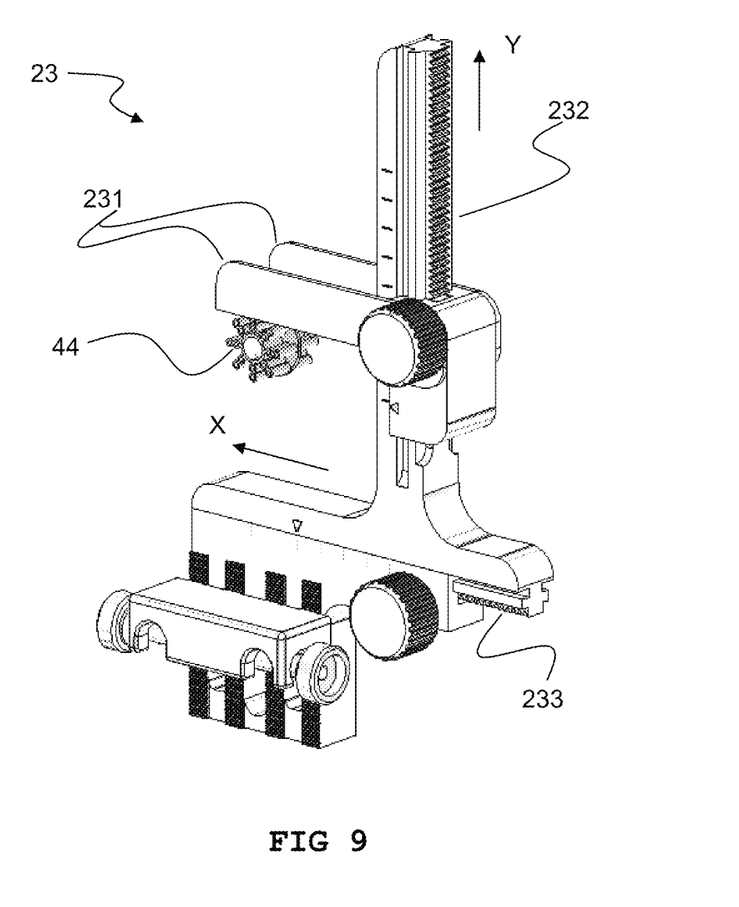
FIG. 9 represents an embodiment of a mechanical stand for positioning bipolar helical electrode assemblies in setups as in FIG. 2.

For correct positioning of the electrode assembly, a mechanical stand 23 for fastening an electrode guiding member 44 of the assembly 40, 400 is preferably used. Referring to FIG. 9, the mechanical stand 23 may comprise a pair of jaws 231 for clamping and/or screwing the guiding member 44 in between and may allow movement of the clamped guiding member 44 in two orthogonal directions, as with an XY table. Therefore, mechanical stand 23 may comprise a couple of linear guides 232, 233 arranged as X and Y to allow movement of the jaws 231 in a plane perpendicular to the axis of guide 22. In an embodiment, the mechanical stand 23 is connected to the motion guide 22 to keep track of any relative movement between the imaging device 50 and the electrode assembly 40, 400.

The guiding member 44 is preferably a guide, which enables the electrodes of the bipolar electrode assembly to pass through it. In an embodiment, a guide, such as ones described above in relation to FIGS. 5-8 is used. The guide 44 may comprise a through-passage formed in accordance with the coils of the helical electrode, such that the helical windings of the electrode pass through the guide by imparting a corkscrew-like movement to the electrode. A function of the guide is to keep the electrode assembly in a fixed position when one is not turning the electrodes, yet to allow relative motion of the electrodes with reference to the guide 44 when inserting the electrodes into the patient (by a corkscrew-like motion in case of helical electrodes). As a result, the guide 44 is a fixed reference point of the electrode assembly. In an embodiment, the guide 44 comprises means 9 for clamping it in mechanical stand 23.

In an example embodiment, step 107 comprises inserting at least the outer helical electrode 41, or 410, and possibly also the inner electrode 42, or 420 through the guide 44 until the tip 411 of the outer electrode 41, 410 reaches the other side of the guide 44. Next, the guide 44 is clamped in mechanical stand 23, which is positioned at the starting position as indicated above.

As already indicated, step 103 may not be performed on the same day as step 107. Therefore, at the onset of steps 105-107 it may be necessary to search with the imaging probe 50 a same position relative to the prostate as during the biopsy procedure. In an example embodiment, step 103 is carried out prior to steps 101, 102 and 104-107. In an embodiment, searching for the same relative position comprises placing the patient in a predetermined position and positioning the imaging device 50 such that the images it captures overlap with the images acquired in step 103 for monitoring the biopsy. By so doing, the original reference is found, and the procedure can continue.

After having positioned the electrode assembly 40 at the starting position as indicated above with reference to step 107, at least the outer electrode of assembly 40 is inserted percutaneously into the prostate in a following step 108. The outer helical electrode 41 or 410 is inserted through the skin into the patient 30 by turning it as with a corkscrew-like movement. The outer electrode 41, 410 may be actuated manually or by an actuator. For manual actuation, the outer helical electrode may be attached to a handle 43 at a proximal end (proximal to the operator performing the procedure), which allows easy turning of the electrode 43. The guide 44 ensures that the outer electrode remains in a correct orientation during the insertion procedure. Hence, during insertion of the helical electrode 41, 410 into the patient 30, guide 44 is held in position by mechanical stand 23.

In an embodiment, and referring to FIG. 4, inner and outer electrodes can be actuated independently of each other, such that the outer electrode 410 may be inserted percutaneously into the patient, while inner electrode 420 remains outside and may be inserted afterwards. The inventor found that inserting the inner electrode afterwards has the advantage of preventing deflection of the inner electrode, in particular in cases where the latter is more flexible than the outer one, during insertion into the patient. It was found that the outer electrode can stabilize the tissue, so that the inner electrode enters the patient's body without deflection. As a result, the two electrodes of assembly 400 are kept in a concentric arrangement all long their length, which increases the precision of the treatment.

In an alternative embodiment, and with reference to FIG. 3, inner and outer electrodes of assembly are fixed to each other, such that the two are inserted simultaneously.

Figure 11:
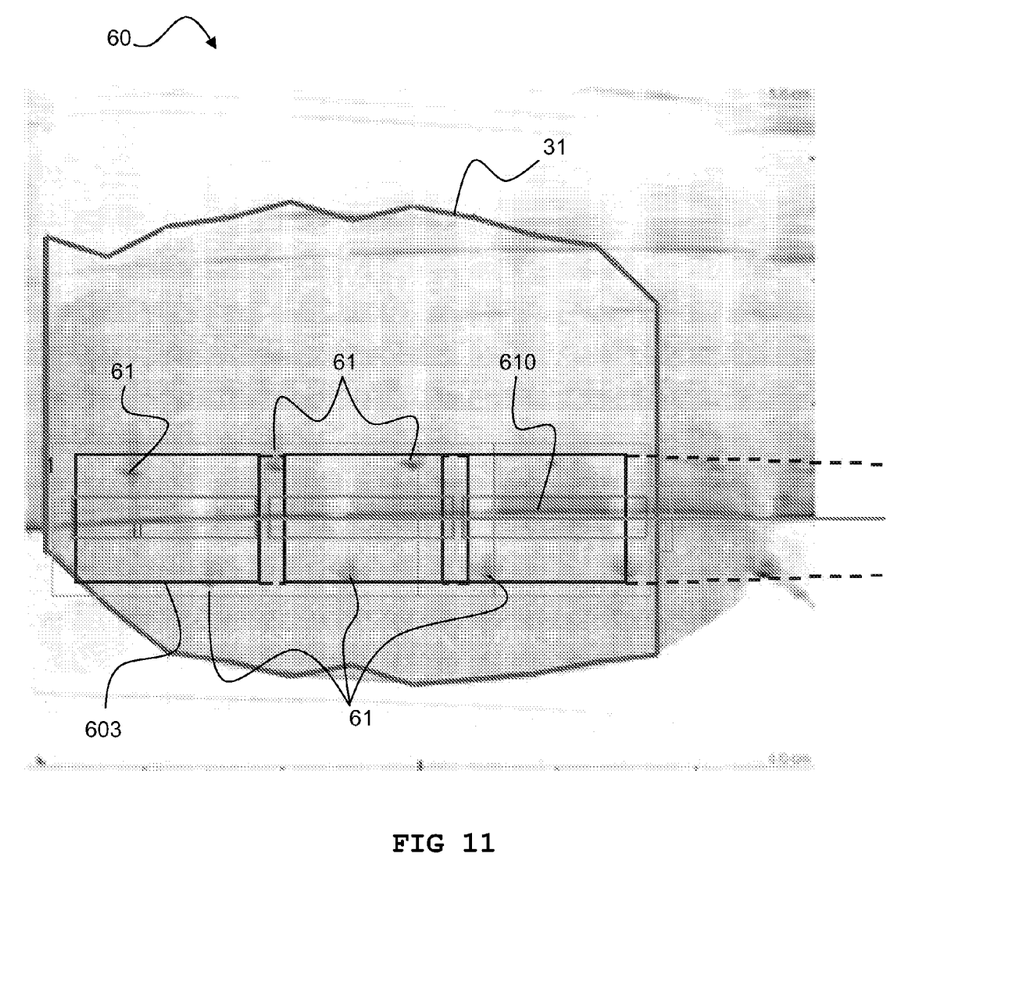
FIG. 11 represents an ultrasound image as in FIG. 10 after insertion of the electrode assembly, such that the actual position of the electrodes is visible on the image.

In a step 109, the (position of the) inserted electrode(s) of assembly 40, 400 is captured, preferably with the imaging device 50, and displayed on the image 60 of the prostate on the graphical display, as shown in FIG. 11. Referring to FIG. 11, there is shown an ultrasound image 60, taken along a longitudinal (sagittal) plane, on which planned target regions 603 and target positions 604 of the inner electrode are represented. Additionally, the actual position of the outer and inner electrodes are visible on the ultrasound image as well. In particular, points of intersection 61 between the outer helical electrode and the plane of the image 60 are visible and give a clear indication of the actual position of the outer helical electrode relative to the planned target position 603. As a result, a direct visual verification of the degree of overlap between the region actually enclosed by the outer electrode and the planned target region is obtained. Similarly, the actual position of the inner electrode, which is a central needle in this case, is visible as a line 610. The actual position 610 of the inner electrode can be very easily compared to the target position 604.

An operator or a computer program may assess/evaluate whether the degree of overlap is satisfactory in a step 110. In an embodiment, a degree of overlap of more than or equal to 75%, or even more than or equal to 90% may be considered satisfactory. In case the degree of overlap is not considered satisfactory, i.e. the actual position of the electrode assembly in the prostate doesn't correspond to the planned target region as desired, the inserted electrode(s) are refracted in a step 111, and the method returns to step 107, for repositioning the bipolar electrode assembly relative to the patient. Thereafter, the method may continue with steps 108-110. This loop may be repeated until a satisfactory degree of overlap is obtained. Repeating steps 111 through 110 does not cause any substantial danger to the patient, since tissue damage is minimum in the meantime.

In an embodiment, a computer program may monitor the advancement of the inserted electrode(s) into the patient in real-time. Based on it, the computer program may calculate the projected final position of the electrode(s) and assess the degree of overlap with the planned target region for treatment.

When the assessment in step 110 is positive, in that a satisfactory degree of overlap is obtained, the method may proceed to step 112, wherein the bipolar electrode assembly 40, 400 is electrically connected to a radio frequency generator (not shown) for applying radio frequency energy to the tissue enclosed within the outer helical electrode 41, 410. Therefore, both the outer electrode 41, 410 and the inner electrode 42, respectively 420 are electrically connected to the radio frequency generator and both act as alternating poles of the bipolar electrode assembly.

Radio frequency energy may be applied for a predetermined period of time and based on medical benchmark tests. The radio frequency energy may be of predetermined intensity (power) based on same benchmark tests.

During application of radio frequency energy, the bipolar electrode assembly is preferably not in motion. The inner and outer electrodes are hence preferably kept still.

Prior to applying radio frequency energy, an impedance measurement between the inserted electrodes may be performed to ensure that the electrodes make contact with tissue. In an embodiment, impedance is monitored while applying radio frequency energy to verify that the ablation treatment is progressing as desired. Where impedance is monitored during ablation treatment, radio frequency power may be adapted based on the measured impedance.

When the inner electrode 42, 420 of assembly 40, 400 is movable independent of the outer electrode 41, 410, the inner electrode may only be inserted after a positive assessment has been carried out in step 110. This avoids unnecessary insertion of the inner electrode.

In an embodiment, the inner electrode 42 is a helical electrode comprising multiple windings of same diameter as shown in FIG. 3. Inner electrode 42 preferably has same pitch as outer helical electrode 41. In an embodiment, inner helical electrode 42 is movable independently of outer electrode 41. Inner electrode 42 is then inserted into the patient after insertion of the outer electrode until it is axially aligned with outer electrode 41 (i.e. until the windings are axially aligned).

In an embodiment, the inner electrode 42, 420 is movable independently of the outer electrode 41, and both electrodes have handles 45 respectively 43 as shown in FIGS. 2 and 4.

Preferably, the electrodes are not hollow, in that they do not comprise any fluid passages for delivering a liquid to the patient's body. Surgical treatments of the present invention advantageously do not comprise any injection of conductive liquid to the region to be treated.

The present invention hence enables to give a precise outcome of the accuracy of the correspondence between the region of the prostate that will be destroyed and the region of the prostate that one plans to destroy. This can be done before doing any damage to the tissue and is made possible by method steps as indicated and by the use of bipolar radio frequency ablation. Indeed, numerous tests carried out by the inventor show that bipolar helical electrode assemblies having an inner electrode and an outer helical electrode allow to confine the region that is ablated (destroyed) to the (cylindrical) volume delimited by the outer helical electrode. The transition zone between the ablated zone and healthy tissue is less than 1 mm thick (see e.g. Richstone et al., "Ablation of Bull Prostate Using Novel Bipolar Radiofrequency Ablation Probe", Journal of Endourology. January 2009, 23(1): 11-16).

As a significant advantage, the present invention enables to obtain on a same image a visualization of both the extent of the planned target region and the extent of the region that will actually be ablated. Since the two are superposed, a verification of the degree of overlap can be carried out prior to starting the treatment. As a result, methods of the invention enable to let coincide the region that is destroyed with the region that was planned to be destroyed. Tissue ablation is hence safely delimited to only a part of the prostate with very limited risk to damage surrounding tissues, like the rectum, pudendum nerves or the urethra.

As another significant advantage, the present invention gives the surgeon and any operator allowed to perform parts of the treatment a planning tool enabling to accurately predict in advance the outcome of the treatment.

What has been described above includes exemplary implementations of the present invention. One of ordinary skill in the art will recognize that many further combinations and permutations of the present invention are possible. Accordingly, the present invention is intended to embrace all such alterations, modifications and variations that fall within the spirit and scope of the appended claims interpreted in accordance with the breadth to which they are fairly, legally and equitably entitled.

What is claimed is:

1. A method of percutaneous treatment of a prostate lesion using radio frequency, comprising:

with an imaging device, acquiring an image of a patient's prostate;

identifying within the patient's prostate at least one location to be treated;

selecting a bipolar electrode assembly for radio frequency treatment, the assembly comprising an outer helical electrode and an inner electrode arranged concentric with the outer helical electrode;

representing a planned target region on the image of the patient's prostate, comprising a graphical representation of at least an active part of the outer helical electrode superimposed on the image at a target position, wherein the planned target region encloses at least in part the at least one location to be treated;

positioning the bipolar electrode assembly in proximity of a patient's perineum, comprising positioning a guiding member in proximity of the patient's perineum, the guiding member comprising an outer member, an inner member, a first through-passage between the outer member and the inner member, and a second through-passage arranged through the inner member;

determining an external starting position of the bipolar electrode assembly outside the patient by projecting the graphical representation along a direction of insertion;

positioning the guiding member according to the graphical representation projecting along the direction of insertion;

disposing the outer helical electrode in the first through-passage and inserting the outer helical electrode percutaneously into the patient's prostate;

disposing the inner electrode through the second through-passage, and inserting the inner electrode percutaneously into the patient's prostate;

wherein the guiding member maintains a position outside the patient during insertion of the outer helical electrode and the inner electrode; and capturing the outer helical electrode that is inserted into the patient's prostate with the imaging device and then displaying the outer helical electrode with the planned target region on the image of the patient's prostate so as to obtain a direct verification of a degree of match between a position of the outer helical electrode and the planned target region.

2. The method of claim 1, wherein the displaying the outer helical electrode with the planned target region on the image of the patient's prostate is represented by image fusion on a graphical display, so that the degree of match can be visually verified.

3. The method of claim 1, wherein the graphical representation is representative of the area or volume enclosed by at least the active part of the outer helical electrode.

4. The method of claim 1, wherein the at least one location to be treated is represented on the image of the patient's prostate.

5. The method of claim 1, comprising extracting, repositioning and re-inserting the outer helical electrode into the patient's prostate.

6. The method of claim 1, wherein the imaging device is an ultrasound imaging device.

7. The method of claim 1, wherein in the bipolar electrode assembly, the inner electrode is a helical electrode arranged concentrically with the outer helical electrode and wherein the helix of the outer helical electrode and the helix of the inner electrode have the same pitch and different diameters.

8. The method of claim 1, wherein in the bipolar electrode assembly, the inner electrode is a straight needle arranged concentrically with the outer helical electrode.

9. The method of claim 1, wherein the inner electrode is inserted after insertion of the outer helical electrode.

10. The method of claim 2, comprising: assessing by a computer program the degree of match, and inserting the inner electrode thereafter.

11. The method of claim 1, wherein the outer helical electrode and the inner electrode are not hollow.

12. The method of claim 1, comprising electrically connecting the bipolar electrode assembly to a radio frequency generator and applying radio frequency energy after insertion of the outer helical electrode and the inner electrode into the patient's prostate, wherein during the application of radio frequency energy, the outer helical electrode and the inner electrode are not in movement.

13. The method of claim 1, wherein the step of identifying within the patient's prostate at least one location to be treated comprises:

performing a biopsy at one or more locations within the patient's prostate; and with the imaging device, acquiring the position of said one or more locations;

and wherein the said one or more locations to be treated comprises at least one location having a positive biopsy result.

14. The method of claim 1, wherein the graphical representation is representative of at least one of a diameter or a length of the active part of the outer helical electrode.

15. A method of percutaneous treatment of a prostate lesion of a patient by applying radio frequency energy by means of a bipolar electrode assembly comprising an outer helical electrode, an inner electrode and a guiding member;

wherein the inner electrode is arranged concentric with the outer helical electrode;

wherein the guiding member comprises an outer member, an inner member, a first through-passage between the outer member and the inner member, and a second through-passage through the inner member;

wherein prior to applying radio frequency energy, the outer helical electrode is disposed in the first through-passage and is inserted percutaneously into the patient's prostate, and the inner electrode is disposed in the second through-passage and is inserted percutaneously into the patient's prostate, wherein the guiding member maintains a position outside the patient during insertion of the outer helical electrode and the inner electrode;

wherein an image of the patient's prostate and of the outer helical electrode as inserted is acquired, such that the outer helical electrode is visualized on the image of the patient's prostate; and wherein a graphical representation of at least an active part of the outer helical electrode is superimposed on the image of the patient's prostate at a target position to obtain a planned target region;

wherein prior to insertion of the outer helical electrode:
a first image of the prostate is acquired;
the graphical representation is superimposed on the first image at the target position;
an external starting position of the bipolar electrode assembly outside the patient is determined by projecting the planned target region along a direction of insertion of the bipolar electrode assembly; and
the guiding member is positioned at the external starting position.

16. The method of claim 15, wherein a guiding member is positioned at the external starting position, the guiding member comprising through-passages fitting corresponding electrodes of the bipolar electrode assembly, such that the electrodes are movable relative to the guiding member and along the through-passages, and wherein the through-passages are aligned with the direction of insertion of the bipolar electrode assembly.

17. The method of claim 15, wherein the graphical representation is representative of a region having the same diameter and/or same length as the active parts of the outer helical electrode.

18. The method of claim 15, wherein the inner electrode is inserted percutaneously into the patient's prostate after insertion of the outer helical electrode.

19. The method of claim 1, wherein a direction of insertion is parallel to an orientation of the imaging device.

* * * * *